US010823805B2

(12) United States Patent
Bydder et al.

(10) Patent No.: US 10,823,805 B2
(45) Date of Patent: Nov. 3, 2020

(54) METHOD AND MAGNETIC RESONANCE APPARATUS FOR IMAGE RECONSTRUCTION WITH TRIMMED AUTOCALIBRATING K-SPACE ESTIMATION BASED ON STRUCTURED MATRIX COMPLETION

(71) Applicants: Centre National de la Recherche Scientifique (CNRS), Paris (FR); Aix-Marseille Universite-TIMONE, Marseilles (FR)

(72) Inventors: Mark Bydder, Marseilles (FR); Olivier Girard, Marseilles (FR); Stanislas Rapacchi, Marseilles (FR)

(73) Assignees: CENTRE NATIONAL DE LA RECHERCHE SCIENTIFIQUE (CNRS), Paris (FR); UNIVERSITÉ D'AIX-MARSEILLE, Marseilles (FR)

( * ) Notice: Subject to any disclaimer, the term of this patent is extended or adjusted under 35 U.S.C. 154(b) by 403 days.

(21) Appl. No.: 15/711,438

(22) Filed: Sep. 21, 2017

(65) Prior Publication Data
US 2019/0086501 A1 Mar. 21, 2019

(51) Int. Cl.
*G01R 33/561* (2006.01)
*G01R 33/48* (2006.01)
(Continued)

(52) U.S. Cl.
CPC ..... *G01R 33/5616* (2013.01); *G01R 33/4818* (2013.01); *G01R 33/565* (2013.01);
(Continued)

(58) Field of Classification Search
CPC ............ G01R 33/5616; G01R 33/4818; G01R 33/5608; G01R 33/5611; G01R 33/565;
(Continued)

(56) References Cited

U.S. PATENT DOCUMENTS

2003/0076988 A1* 4/2003 Liang ................ G06T 5/10
382/131
2015/0078489 A1* 3/2015 Zhu .................. H03M 7/3062
375/340
(Continued)

FOREIGN PATENT DOCUMENTS

CN 104156994 B * 3/2017

OTHER PUBLICATIONS

Machine Translation of CN104156994B (Year: 2017).*
(Continued)

*Primary Examiner* — Amelie R Davis
*Assistant Examiner* — John Denny Li
(74) *Attorney, Agent, or Firm* — Schiff Hardin LLP

(57) ABSTRACT

In a method and magnetic resonance (MR) apparatus for MR image reconstruction, an image reconstruction algorithm is used that operates on one calibration matrix that is formed by reorganizing a number of individual, undersampled k-space data sets respectively acquired by multiple reception coils in a parallel MR data acquisition from a subject exhibiting motion. The motion causes the k-space data sets to exhibit errors. In order to use the calibration matrix in the reconstruction algorithm, it is subjected to an iterative rank reduction procedure in which, in each iteration, a residual is calculated for each data point that represents how poorly, due to motion-induced corruptions, that data point satisfies the low rank constraint, and non-satisfying data points are removed from the data point for the next iteration. The resulting low rank matrix at the end of the iterations is then used to produce images with fewer motion-induced errors.

24 Claims, 6 Drawing Sheets

(51) Int. Cl.
| | |
|---|---|
| *G06T 11/00* | (2006.01) |
| *G06T 5/00* | (2006.01) |
| *G01R 33/56* | (2006.01) |
| *G01R 33/565* | (2006.01) |
| *G06F 19/00* | (2018.01) |
| *G16H 50/70* | (2018.01) |
| *G16H 30/40* | (2018.01) |

(52) U.S. Cl.
CPC ...... *G01R 33/5608* (2013.01); *G01R 33/5611* (2013.01); *G01R 33/56509* (2013.01); *G06F 19/321* (2013.01); *G06T 5/001* (2013.01); *G06T 11/005* (2013.01); *G16H 30/40* (2018.01); *G16H 50/70* (2018.01)

(58) Field of Classification Search
CPC .. G01R 33/56509; G16H 50/70; G16H 30/40; G06F 19/321; G06T 5/001; G06T 11/005
See application file for complete search history.

(56) References Cited

U.S. PATENT DOCUMENTS

| | | | | |
|---|---|---|---|---|
| 2016/0267689 | A1* | 9/2016 | Ye | G06T 11/008 |
| 2016/0363644 | A1* | 12/2016 | Wang | G01R 33/58 |
| 2018/0322228 | A1* | 11/2018 | Kumar | G03F 1/36 |
| 2019/0086498 | A1* | 3/2019 | Zheng | G01R 33/5612 |

OTHER PUBLICATIONS

Haldar, Justin P.: "Low-Rank Modeling of Local k-Space Neighborhoods (LORAKS) for Constrained MRI"; in: IEEE Transactions on Medical Imaging; vol. 33; No. 3; pp.668-681; Mar. 2014; DOI: 10.1109/TMI.2013.2293974.

Jensen, Soren H. et al.: "Reduction of Broad-Band Noise in Speech by Truncated QSVD"; in: IEEE Transactions on Speech and Audio Processing; vol. 3; No. 6; pp.439-448; 1995.

Bydder, Mark et al. "Detection and Elimination of Motion Artifacts by Regeneration of k-Space" Magnetic Resonance in Medicine, vol. 47, pp. 677-686, 2002 // DOI: 10.1002/mrm.10093.

Zhang, Jian et al.: "Parallel Reconstruction Using Null Operations"; in: Magnetic Resonance in Medicine; vol. 66; No. 5; pp. 1241-1253; Nov. 2011; doi: 10.1002/mrm.22899.

Nielsen, Tim et al.: "Self-Consistency Driven Data Rejection for Reduction of Motion Artifacts"; ISMRM Workshop on Motion Correction in MRI; 2014.

Lee D et al, Acceleration of MR parameter mapping using annihilating filter-based low rank Hankel matrix (ALOHA); Magn Reson Med 2016; 76:1848; 2016.

Markovsky, Ivan et al.: "Structured low-rank approximation and its applications"; in: Automatica; vol. 44; pp.891-909; 2008; doi: 10.1016/j.automatica.2007.09.011.

Campbell-Washburn AE et al; Using the robust principal component analysis algorithm to remove RF spike artifacts from MR images; Magn Reson Med; 2016; 75:2517; 2016.

Anderson Ashley G et al; Adaptive retrospecitve correction of motino artifacts in cranial mri with multicoil three-dimensional radial acquisitions; Magn Reson Med; 2013; 69:1094; 2013.

Gillard, Jonathan et al.: "Cadzow's basic algorithm, alternating projections and singular spectrum analysis"; in: Statistics and Its Interface; vol. 3; pp.335-343; 2010.

Shin, Peter J. et al: "Calibrationless Parallel Imaging Reconstruction Based on Structured Low-Rank Matrix Completion"; in: Magnetic Resonance in Medicine; vol. 72; pp. 959-970; 2014; DOI 10.1002/mrm.24997.

Bydder, Mark et al.: "Partial Fourier Partially Parallel Imaging"; in: Magnetic Resonance in Medicine; vol. 53; pp.1393-1401; 2005; DOI: 10.1002/mrm.20492.

Derbyshire, John A.: "Golden-step phase encoding for flexible realtime Cardiac MRI"; in: Journal of Cardiovascular Magnetic Resonance; vol. 13 (Suppl 1); P23; 2011.

Atkinson David, et.al. :"Automatic Compensation of Motion Artifacts in MRI", in: Magnetic Resonance in Medicine vol. 41, pp. 163-170, 1999; 1999.

Zaitsev, Maxim et al.: "Motion Artifacts in MRI: A Complex Problem With Many Partial Solutions"; in: Journal of Magnetic Resonance Imaging; vol. 42; Issue 4; pp.887-901; 2015; DOI: 10.1002/jmri.24850.

Andreychenko, A. et al.: "Thermal noise variance of a receive radiofrequency coil as a respiratory motion sensor"; in: Magnetic Resonance in Medicine; vol. 77; Issue 1; pp. 221-228; 2017; DOI: 10.1002/mrm.26108.

Weick, Stefan et al.: "Desynchronization of Cartesian k-Space Sampling and Periodic Motion for Improved Retrospectively Self-Gated 3D Lung MRI Using Quasi-Random Numbers"; in: Magnetic Resonance in Medicine; vol. 77; pp.787-793; 2017; DOI: 10.1002/mrm.26159.

Huber, Peter J.: "Robust Statistics"; 2nd Edition; 2009; Wiley Verlag; DOI: 10.1002/9780470434697.fmatter.

Hilbert, Tom et al.: "Phase-Encode Ghosting Detection using Multi-Channel Coil Arrays"; in: Proc. Intl. Soc. Mag. Reson. Med.; vol. 24; 1829; 2016.

Lustig, M. et al: Iterative Self-consistent Parallel Imaging Reconstruction From Arbitrary k-Space2; in: Magnetic Resonance in Medicine; vol. 64; pp. 457-471; 2010.

Jin, Kyong Hwan et al.: "MRI Artifact Correction Using Sparse 1 Low-Rank Decomposition of Annihilating Filter-Based Hankel Matrix"; in: Magnetic Resonance in Medicine; vol. 78; pp.327-340; 2017; DOI: 10.1002/mrm.26330.

Samsonov et al.: "POCS-Enhanced Correction of Motion Artifacts in Parallel MRI"; in: Magn Reson Med.; 63.4; 2010; pp.1104-1110. Print.

Beck, Amir et al.: "Weiszfeld's Method: Old and New Results"; in: Journal of Optimization Theory and Applications; vol. 164; pp. 1-40; 2015; DOI: 10.1007/s10957-014-0586-7.

* cited by examiner

METHOD AND MAGNETIC RESONANCE APPARATUS FOR IMAGE RECONSTRUCTION WITH TRIMMED AUTOCALIBRATING K-SPACE ESTIMATION BASED ON STRUCTURED MATRIX COMPLETION

BACKGROUND OF THE INVENTION

Field of the Invention

The present invention relates to methods and systems for reconstructing image data from acquired magnetic resonance (MR) data that are entered into k-space in order to form a k-space matrix, the method and apparatus being of the type wherein the reconstruction makes use of a structured matrix completion algorithm. The invention also encompasses a computer programmed to implement such a method, and a non-transitory data storage medium encoded with programming code that cause a computer to implement such a method.

Description of the Prior Art

Parallel imaging is a known technique in magnetic resonance imaging wherein the raw MR data are acquired by a number of individual reception coils, in order to reduce the overall scanning time. Because each coil receives MR data from only a portion of the total region of the subject to be imaged, each coil's data set is undersampled, i.e., not every available point in k-space is filled with a data entry. Moreover, the acquired data are dependent on the location of the respective coil. For these reasons, special image reconstruction algorithms must be used in the case of parallel imaging.

Known techniques such as SMASH and SENSE require that the image reconstruction computer, in addition to the acquired raw data, be provided with calibration data that represents the respective sensitivity profiles of the reception coils. This requires that a calibration data acquisition procedure be conducted in addition to the diagnostic data acquisition procedure.

Other techniques, known as autocalibrating methods avoid the need for a separate calibration data acquisition, by including autocalibration signals in the acquired data, as a fully sampled center of k-space together with undersampled higher frequency k-space regions. Such autocalibrating methods generate sensitivity images from the autocalibration signals. Known techniques such as GRAPPA and SPIRIT make a kernel calibration from the autocalibration signals and synthesize data that can be used as the "missing" data that result from the undersampling.

Several recent parallel magnetic resonance imaging (MRI) techniques are based on identifying the nullspace of a "calibration matrix" (Lustig et al., "SPIRIT: Iterative Self-consistent Parallel Imaging Reconstruction From Arbitrary k-Space," Magnetic Resonance in Medicine, Vol. 64, pp. 457-471 (2010); Zhang et al., "Parallel Reconstruction Using Null Operations," Magnetic Resonance in Medicine, Vol. 66, pp. 1241-1253 (2011); Shin et al., "Calibrationless Parallel Imaging Reconstruction Based on Structured Low-Rank Matrix Completion," Magnetic Resonance in Medicine, Vol. 72, pp. 959-970 (2014)). The calibration matrix contains k-space data arranged in a Hankel structure corresponding to convolution with a local kernel over several receiver coils (see FIG. 1). The existence of a non-trivial nullspace (i.e. singular values that are of the same magnitude as the measurement noise) implies linear dependencies between the data points and hence that every point can be replicated by a linear combination of neighboring points. This redundancy is the basis of scan time reductions in parallel imaging since k-space points that can be generated from other k-space points do need not to be acquired.

The nullspace is obtained by singular value decomposition (svd) of the calibration matrix $$A = USV^H \tag{1}$$

where the columns in V corresponding to "small" values in S are basis vectors of the nullspace. As an example, with a dataset of 8 coils and a convolution kernel of 5×5, the matrix V would be 200×200 in size (i.e. 8×5×5) and about half the columns would represent the nullspace (see FIG. 1).

Knowledge of the nullspace vectors permits recovery of a full k-space from one that has been undersampled to reduce scan time. Undersampling leaves unfilled entries in k-space and reduces the number of points to which the convolution kernel can be validly applied. The remaining points are called the calibration (or autocalibration) data. Excessive undersampling can lead to a total loss of calibration data and an unrecoverable problem when the number of rows of A becomes zero.

According to the aforementioned articles by Lustig et al. and Zhang et al., the recovery of a full k-space (k) from the acquired data (y) can be posed as a regularized least squares problem $$\begin{bmatrix} D \\ G_v \\ \ldots \end{bmatrix} k = \begin{bmatrix} y \\ 0 \\ \ldots \end{bmatrix} \tag{2}$$

where D is a matrix representing data sampling (e.g. diagonal with a 1 or 0 on the diagonal for Cartesian sampling) and $G_v$ are matrices representing convolution with kernels composed of the $v^{th}$ nullspace vector. Eq 2 is of the order $10^7 \times 10^5$ in size (10 Tb) and therefore impractical to construct; however, matrices D and $G_v$ can be applied as sparse operations and convolutions so Eq 2 can be solved in a few seconds by iterative gradient descent.

The constraint matrices in Eq 2 require that certain linear combinations of points be nulled, i.e. $\|G_v k\| \approx 0$ for all v in the nullspace. This same constraint can be used as a way to detect inconsistencies in the data caused by patient motion during the scan, since motion causes phase shifts and rotations in the data that violate the nulling criteria. The idea has been used previously with various parallel imaging methods used to exploit the redundancy (Bydder et al., "Detection and Elimination of Motion Artefacts by Regeneration of K-space," Magn Reson Med, Vol. 47, pp. 677-686 (2002); Samsonov et al., "POCS-enhanced correction of motion artifacts in parallel MRI," Magn Reson Med., Vol. 63(4), pp. 1104-10 (2010); Nielsen et al., "Self-consistency driven data rejection for reduction of motion artefacts," ISMRM WORKSHOP on Motion Correction in MRI (2014); Hilbert et al., "Phase-Encode Ghosting Detection using Multi-Channel Coil Arrays," ISMRM, p. 1829 (2016)); while the specific implementation details differ, these methods essentially solve an equation similar to Eq 2 (e.g. by least squares)

$$\hat{k} = \left( D^H D + \sum_v G_v^H G_v \right)^{-1} D^H y \tag{3}$$

and then use the solution to calculate a residual.

$$r = \begin{bmatrix} D \\ G_v \\ \ldots \end{bmatrix} \hat{k} - \begin{bmatrix} y \\ 0 \\ \ldots \end{bmatrix} \quad [4]$$

The elements in the vector r provide a way to identify and penalize grossly ill-fitting data points, e.g. by rejecting or weighting in proportion to $|r|^{-1}$. This is the basis of the iteratively reweighted least squares (IRLS) algorithm which was proposed as a way to mitigate gross errors in k-space (Bydder et al., "Partial Fourier partially parallel imaging," Magn. Reson. Med., Vol. 53, pp. 1393-1401 (2005)). While the approach seems straightforward, the results can be unsatisfactory in practice for several reasons.

Firstly, the matrices $G_v$ are usually derived from a subset of data at the center of k-space (the calibration data). This requires the calibration data to be free of motion errors or otherwise leads to an errors-in-variables problem with gross errors in the left- and right-hand sides. This is not amenable to solution by least squares or even IRLS.

Secondly, the consistency criteria $\|G_v k\| \approx 0$ is applied to the solution $\hat{k}$ rather than the raw data y. Since $\hat{k}$ is constructed from linear combinations of y, outliers are spread over multiple points causing a loss of precision. This means that a single outlier in y shows up as multiple inconsistencies in r, even in the case that the calibration data (and $G_v$ matrices) are not corrupted.

Thirdly, the magnitude of r exhibits a dependence on the underlying signal in k-space and the local sampling density. This causes insensitivity at the high spatial frequencies (leading to false retention) and over sensitivity at the low spatial frequencies (leading to false rejection). In accelerated scans in particular this can easily result in rejection of all the calibration data.

SUMMARY OF THE INVENTION

An object of the present invention is to provide an approach to deal with motion corrupted data in an image reconstruction otherwise being implemented as the Simultaneous Autocalibrating and K-space Estimation (SAKE) technique described in the aforementioned article by Shin et al., which is incorporated herein by reference, which in turn derives from matrix completion and structured low-rank matrix approximation (Gillard et al., "Cadzow's basic algorithm, alternating projections and singular spectrum analysis," Statistics and Its Interface, Vol. 3, pp. 335-343 (2010); Markovsky et al., "Structured low-rank approximation and its applications," Automatica, Vol. 44, pp. 891-909 (2008)).

As explained in the Markovsky article, structured low-rank approximation does not presuppose dependent/independent variables, and can tolerate what would be ill-conditioning when expressed in the form of Eq 2.

The inventive approach can be designated as Trimmed Autocalibrating and K-space Estimation (TAKE).

A method for magnetic resonance (MR) image reconstruction, has the following steps.

A computer is provided with undersampled k-space data sets, each having data points in a k-space matrix, in which data entries at those data points were made in each k-space data set by a parallel MR data acquisition from a subject exhibiting motion, using multiple reception coils, with each reception coil sampling (filling) a respective one of the k-space data sets. The motion of the subject causes the data points in each of the k-space data sets to contain errors.

The computer generates one data matrix for an image reconstruction algorithm that uses a parallel image reconstruction technique together with a structured low rank matrix completion of that data matrix, which requires the data matrix to satisfy a low rank matrix constraint, by organizing the data points in the k-space data sets in order to give the data points in the calibration matrix a Hankel structure.

For each said calibration matrix, the computer calculates a noise variance estimation based on the singular values of the calibration matrix.

The computer subjects the calibration matrix to an iterative rank reduction procedure in which the rank of the calibration matrix is reduced in each iteration. After each iteration, the residual is calculated for each data point that is the difference between the reconstructed points and the actual acquired data points. Data points are removed, for a next iteration, that have a residual that is higher than a predetermined residual threshold. The iterations are repeated until a predetermined completion criterion is reached, with a last iteration, in which the completion criterion was reached, producing a low rank calibration matrix.

The computer executes the parallel image reconstruction technique together with the structured low rank matrix completion using the low rank calibration matrix, in order to reconstruct an image data set of the subject, and makes the reconstructed image data of the subject available from the computer in electronic form as a data file.

The invention also encompasses a computer programmed with program code in order to implement such a method, and a magnetic resonance apparatus having a computer system that embodies such a computer or processor.

The invention also encompasses a non-transitory, computer-readable data storage medium encoded with programming instructions (program code) that, when the storage medium is loaded into a computer or computer system, cause the computer or computer system to implement the method according to the invention.

DESCRIPTION OF THE PREFERRED EMBODIMENTS

Figure 1:
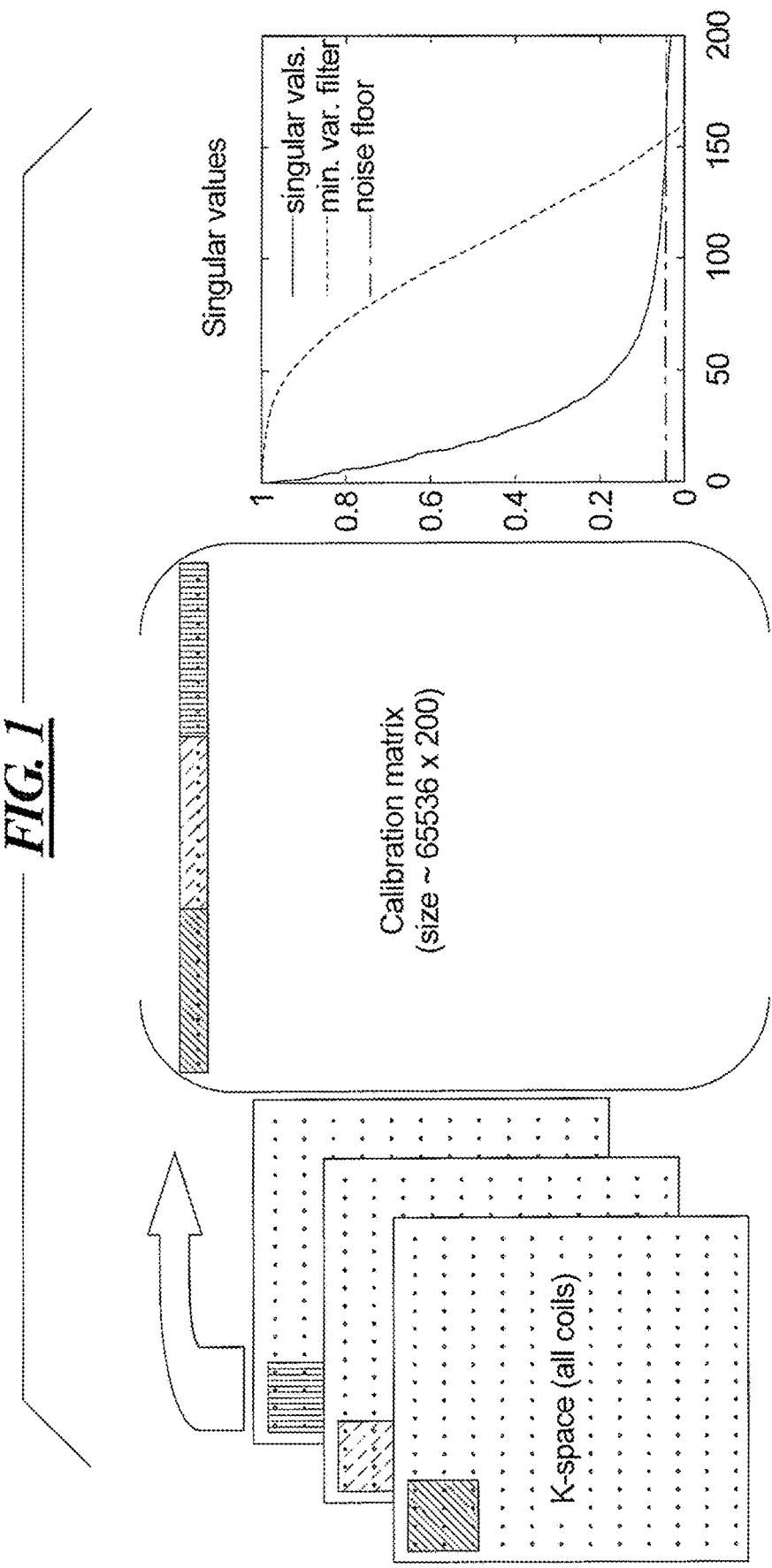
FIG. 1 is a schematic illustration showing the reconstruction of a row of a calibration matrix resulting from a convolution in k-space over multiple coils.

In contrast to virtually every other parallel imaging method, SAKE uses all of the acquired data for calibration rather than a subset of contiguous data at the center of k-space. It does this by constructing a large calibration matrix with zeros inserted in the entries where data are missing. Starting from this (incomplete) matrix, a structured low-rank matrix approximation technique is employed to fill in the gaps (complete the matrix). Over the course of many iterations of projection onto convex sets (POCS), the zeros are replaced with values that cause the calibration matrix to have both Hankel structure (corresponding to convolution with a locally defined kernel) and low rank.

Fundamentally the method works because the zeros are incompatible with low rank. In much the same way, motion corrupted data are also incompatible with low rank. If the corrupted data are removed from the dataset, then the problem simplifies to SAKE with fewer data points. On its own, however, SAKE lacks a mechanism for rejecting inconsistent data. Modifications are introduced in accordance with the invention to extend the SAKE technique so as to achieve a new approach that is robust to such errors.

1. Noise Variance Estimation

The calibration matrix A can be written as the sum of a (low rank) true matrix $\bar{A}$ plus errors E.

$$A = \bar{A} + E \quad [5]$$

For the case that E is Gaussian random noise with standard deviation $\sigma_{noise}$ in the real and imaginary parts, the singular values of A can be written as (Jensen et al., "Reduction of Broad-Band Noise in Speech by Truncated QSVD," IEEE Transactions on Speech and Audio Processing, Vol. 3, pp. 439-448, (1995))

$$\sigma_v = \sqrt{\bar{\sigma}_v^2 + \sigma_{floor}^2} \quad [6]$$

where $\bar{\sigma}_v$ are the (unknown) singular values of $\bar{A}$, $\sigma_{floor}^2 = 2\sigma_{floor}^2 \text{nclos}(A)d$ and $0 < d \leq 1$ is the fraction of nonzeros in A. The presence of outliers perturbs the larger singular values but the smaller singular values are still dominated by $\sigma_{floor}$ which allows for estimation of $\sigma_{noise}$. Conversely, if $\sigma_{noise}$ is known from a separate procedure then $\sigma_{floor}$ can be calculated directly instead of estimated from the singular values. To impose a low rank constraint on A, singular values similar to $\sigma_{floor}$ may be thresholded.

2. Minimum Variance Filtering

Since there is typically no large gap in $\sigma_v$ to demarcate large and small singular values, it can seem arbitrary to set a hard threshold. An alternative is to apply a filter that transitions smoothly between small and large values. One such filter, used for minimum variance estimation (Jensen et al., "Reduction of Broad-Band Noise in Speech by Truncated QSVD," IEEE Transactions on Speech and Audio Processing, Vol. 3, pp. 439-448, (1995)), is defined as in Eq 7.

$$f_v = 1 - \frac{\sigma_{floor}^2}{\sigma_v^2} \quad [7]$$

This filter applied to the singular values of A produces the closest approximation to $\bar{A}$ (in the Frobenius norm) that can be made from a linear combination of the columns of A. Filtering is applied to A by post-multiplication with $F = V \text{diag}(f) V^H$.

3. Robust Location Parameter

The calibration matrix has a Hankel structure that contains many repeated copies of the same data points. After the rank reduction step (or singular value filtering), these copies are no longer identical and must be reconciled in order to preserve the Hankel structure. SAKE takes the mean value, however in the context of outliers the mean is vulnerable and an alternative is preferable.

A standard robust estimator of location is the median (or geometric median in the complex plane), which can be computed by IRLS using the Huber function $w(r) = \min(1, \text{scale}/|r|)$ (Beck et al., "Weiszfeld's Method: Old and New Results," J Optim Theory Appl, Vol. 164, pp. 1-40 (2015)). When the scale parameter$\to 0$ the result is the geometric median (minimizes the distance) and when the scale parameter$\to \infty$ the result is the mean (minimizes the distance squared). The former can converge slowly and so a "medium" scale parameter of around $\sigma_{noise}$ balances robustness and computation time.

4. Trimming Outliers

The above steps produce an estimate for every point in k-space, including those points that were acquired. The difference between the estimate and the acquired points defines a residual R. Note this residual is comparable to the data part of the residual in Eq 4 (i.e. $D\hat{k} - y$) but with $\hat{k}$ determined by the above steps (structured low-rank approximation) rather than by solving a linear equation (Eq 3).

R is a measure of how poorly points satisfy the low-rank constraint. Periodically trimming the data set of the worst points (i.e. those with highest |R|) leads to lower rank calibration matrix. The procedure can be continued until there are no data left and so a stopping rule is required. One choice is to reject a certain predetermined fraction of the data—analogous to the trimmed mean or least trimmed squares—which leads to a trimmed variant of SAKE Accumulating |R| over dimensions that have been acquired simultaneously (or rapidly in comparison to the motion, e.g. coils, readout points, multiple echoes) yields a low dimension projection with spikes where there are gross errors, similar to the "detection plot" of previous studies such as the aforementioned Bydder et al. (2002) and Samsonov et al. articles. Typically this would be a plot of error versus phase encode index. A difficulty with summation is that |R| follows the signal distribution in k-space so low frequencies tend to have high amplitude and high frequencies have low amplitude. Principal component analysis (pca) over R (using the first component only) can help to reduce this confounding effect.

5. Separate Calibration

A common approach in parallel imaging is to use calibration data from a separate acquisition. The calibration data are used to find the nullspace which then provides the regularization matrices ($G_v$). In the case of TAKE, separate calibration data may be incorporated by constructing a second calibration matrix C, identical in structure to A, and concatenating the two.

$$A \to \begin{bmatrix} A \\ C \end{bmatrix} \quad [8]$$

The reconstruction may be performed with this new calibration matrix to recover both A and C. However, if it can be assumed there are no errors in C then there is no need to trim data from C and it is computationally expedient to perform the svd (singular value decomposition) on $C = USV^H$ instead of A. This means that the rank reducing transform (post-multiplication by F) will be applied along the axes for which A should have negligible component, which accelerates convergence. Taking the svd operation outside the iterative loop substantially reduces the computation burden.

6. Combination With Others Constraints

Redundancy in the acquisition is expressed as low rankness in the calibration matrix. One source of the redundancy is multiple array coils however other types of redundancy may be exploited to expose low rank. Two examples are object support in the spatial domain and conjugate symmetry in the k-space domain. As explained in (Haldar et al., "Low-rank modeling of local k-space neighborhoods (LORAKS) for constrained MRI," IEEE Trans Med Imaging, Vol. 33(3), pp. 668-81 (2014))), the object support constraint is expressible as a local k-space convolution in the same way as parallel imaging and hence is already implicit in the calibration matrix. On the other hand, conjugate symmetry requires additional modifications.

A way to expose the low rankness inherent in conjugate symmetry is to concatenate the calibration matrix with a conjugated and permuted copy of itself.

$$A \to |AP\bar{A}| \qquad [9]$$

where the overbar represents complex conjugation and P is a permutation matrix that ensures that every row of A is paired with its conjugate symmetric counterpart in $\hat{A}$.

The reconstruction may be performed with this new calibration matrix, which has two times the redundancy of the original matrix and can tolerate a greater proportion of missing data (whether by undersampling or by data rejection).

Other forms of redundancy may be use when written in terms of a low rank matrix constraint. Such examples may include spatial smoothness, sparseness of a transform of the image (such as the derivative or wavelet transform) or similarity with a reference image.

Methods

Experiments were performed on a 3T scanner (Siemens, Erlangen, Germany). A 2D spin echo sequence was performed with a 4 channel head coil, TR/TE=500/10, bandwidth 500 Hz/pixel, matrix 256×256, in-plane resolution 1 mm and slice thickness 3 mm. Complex raw data was taken offline and all reconstructions were performed in single precision using MATLAB 2016a (Natick, Mass.) with GPU acceleration (NVIDIA Quadro K2200).

A useful speedup technique is to perform svd on the normal matrices, which returns the same matrix V and the square of the singular values as compared with the original matrix. This reduces the numerical precision but is tolerable at the signal to noise ratios (SNR) of MRI data (2-3 significant digits). Reconstruction times were around 0.2 sec per iteration) with the majority of time spent constructing and deconstructing A (the circshift function).

Parameters for SAKE and TAKE reconstructions were: kernel size 7×7, IRLS scale factor $\sigma_{noise}$, number of IRLS iterations 3, trim every 100 iterations, trim ~20% of the data. Parameters for the nullspace/IRLS reconstructions based on Eq 2-4 (comparable to SPIRIT or PRUNO) were: kernel size 7×7, center±12 lines used for calibration, iterations 300, svd threshold 0.1 of the maximum singular value, trim the highest residual line every iteration of IRLS. This approach can be considered representative of previous implementations of parallel imaging reconstruction that incorporate a data rejection step, as exemplified by the aforementioned articles by Bydder et al., Samsonov et al., Nielsen et al., Hilbert et al., and the article (Bydder et al., "Partial Fourier partially parallel imaging," Magn. Reson. Med., Vol. 53, pp. 1393-1401 (2005)).

Results

Figure 2:
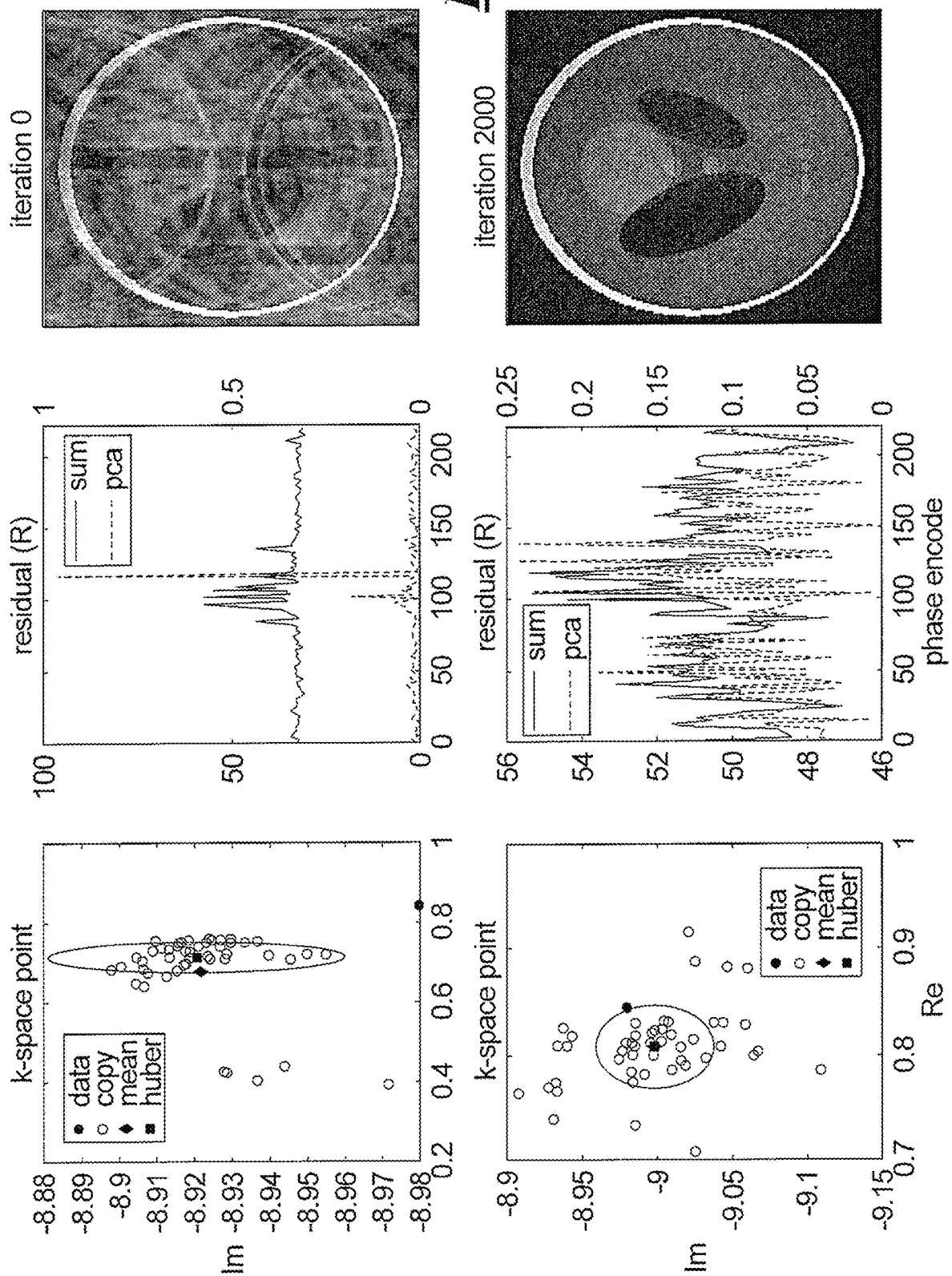
FIG. 2 illustrates the example of a Shepp Logan phantom from eight coils, with an acceleration factor of 1.6, and simulated translation errors mimicking patient motion during the scan.

FIG. 2 presents simulation results from an 8-channel Shepp-Logan phantom with a small amount of added Gaussian random noise (SNR ~25). The dataset was sub-sampled in one direction to effect a 2-fold speedup with a contiguous region of 25 k-space calibration lines (total 122 out of 220). The center of k-space was at line 110.

The dataset was contaminated with phase errors in lines 5, 7, 23, 27, 41, 79, 85, 95, 97, 102, 103, 107, 109, 110, 117, 135, 205, 211 (total of 18 lines) making sure to corrupt multiple calibration lines. The TAKE process was performed for 2000 iterations with a total of 20 rejections; of those, all errors were detected except line 41, which was a false retention, and lines 113, 119 and 121 were false rejections.

In the left-side panel of FIG. 2, the oval shape is in fact a circle with radius $\sigma_{noise}$. Note the majority of the copies are clustered within 1-2 $\sigma_{noise}$ but there are several outliers at more than 5 $\sigma_{noise}$; at the end of the iterations these outliers are no longer present reflecting that most of the corrupted data have been removed. The Huber estimator is more computationally expensive than the mean but can reduce the influence of distant points when combining the copies into a single estimate.

The final image has some minor remaining artefacts, which may be due to line 41 or the complicated aliasing/g-factor noise pattern from the resultant uneven sampling pattern of the trimmed dataset.

Figure 3:
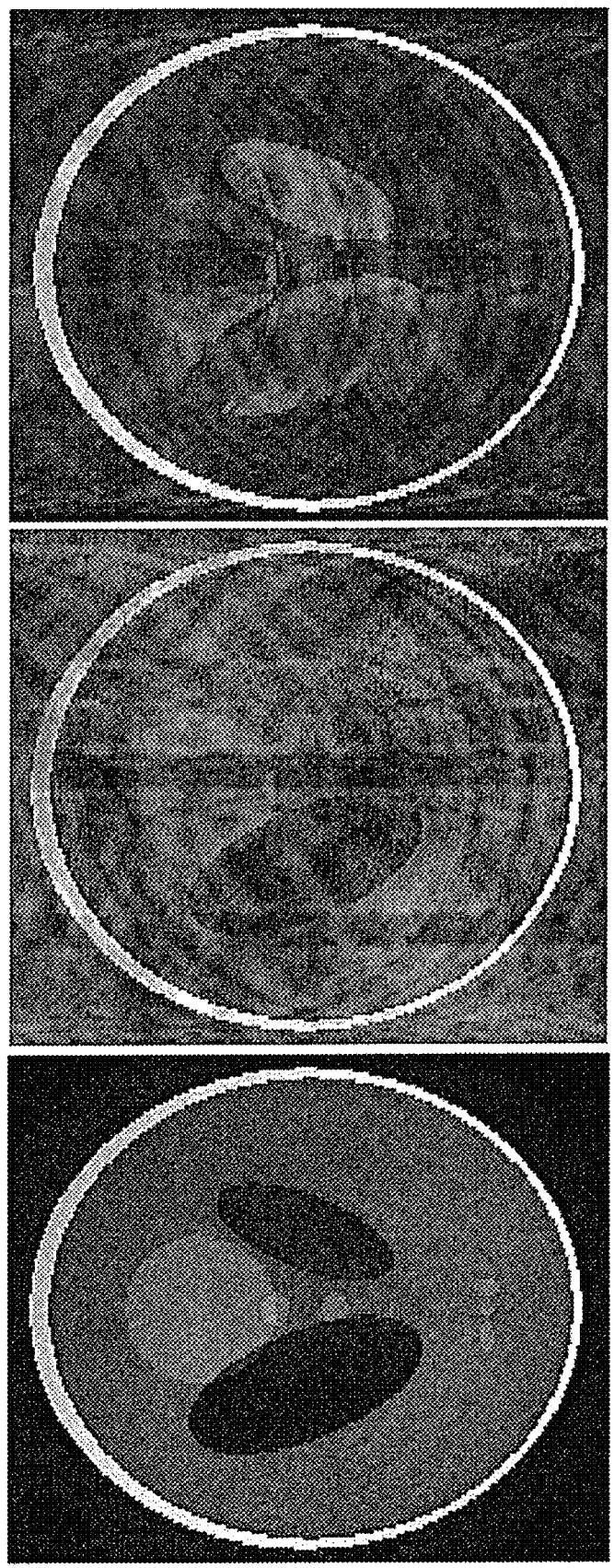
FIG. 3 shows reconstructed image from the data set of FIG. 2, using 2000 iterations of TAKE, SAKE, and seven iterations of IRLS.

FIG. 3 shows reconstructions from the same data set as FIG. 2 but using SAKE or Eq 2-4 with IRLS rejection of the highest residual data points. The results show that SAKE with the same number of iterations (2000) does not reduce the influence of gross errors. The IRLS method rejected lines 97, 102, 107, 109, 110, 111, 117 at which point (on iteration 7) the problem became unrecoverable due to a lack of calibration data.

Figure 4:
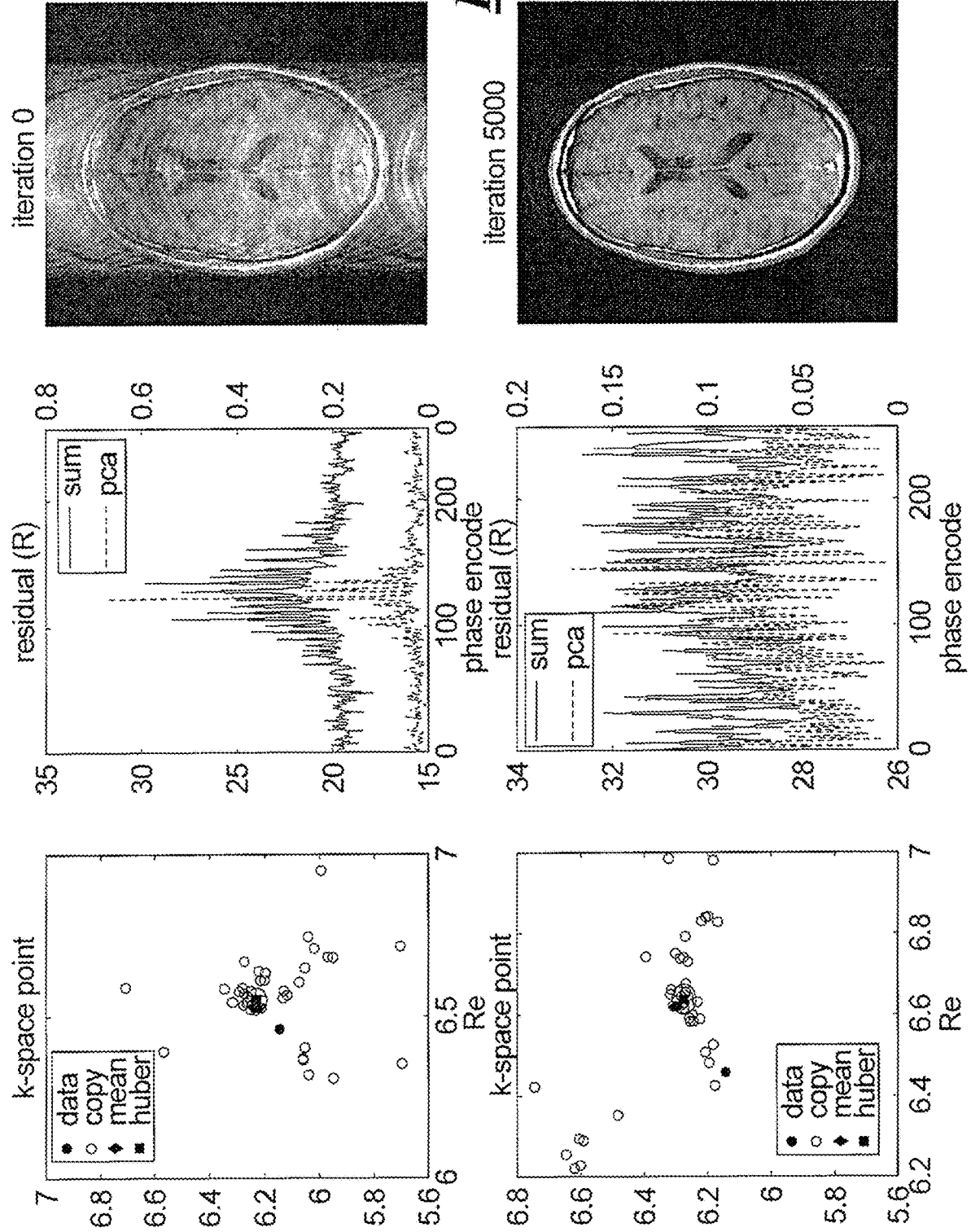
FIG. 4 illustrates an image of a volunteer scanned with motion corruption using a 4 channel head coil, and an acceleration factor of 1.0, wherein the images correspond to those described in FIG. 2.

FIG. 4 shows an example from a volunteer using a 2D T1-weighted spin echo sequence with a fully sampled data set (total of 256 out of 256 lines). The center of k-space was at line 129. The volunteer was asked to move throughout the scan every few seconds by either lifting or rotating the head and then returning to the original position.

The panels show plots of a complex k-space point near the center of k-space, the residual and the images at the beginning and end of the iterations. After 5000 iterations, 50 lines were rejected including lines 117, 118, 123, 124, 126, 129, 130, 132, 134, 136, 137, 139, 141 (nominally in the calibration data region, i.e. ±12 lines at the center of k-space). A substantial reduction in artifacts was observed albeit not as complete as compared to the numerical phantom. This may reflect several non-idealities with real motion, namely that the corruption did not affect isolated k-space lines but several consecutive lines, and that the return to the original position was only approximate. The plot of a k-space point near the center of k-space shows that even on the last iteration there are many points at a distance greater than 5 $\sigma_{noise}$, which presumably reflects some remaining gross errors.

Figure 5:
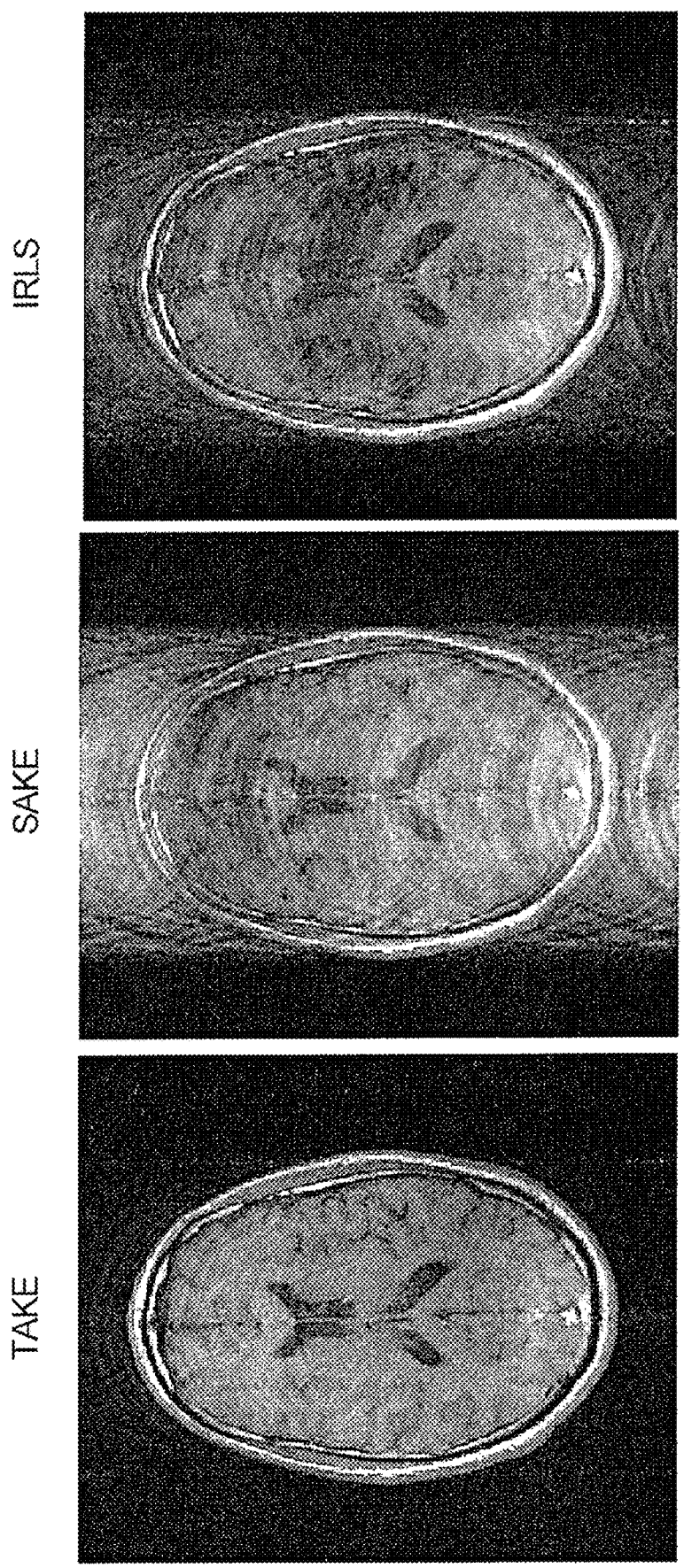
FIG. 5 shows reconstructed images from the data set used in FIG. 4, using 5000 iterations of TAKE, SAKE, or 6 iterations of IRLS.

FIG. 5 shows reconstructions from the same data set as FIG. 4 but using SAKE or Eq 2-4 with IRLS rejection of the highest residual data points. The IRLS rejected lines 107, 128, 129, 130, 131, 136 at which point (on iteration 6) the problem became unrecoverable due to a too large a gap in k-space (gap>number of coils). As with FIG. 3, these results show that SAKE alone does not mitigate gross errors and that IRLS can be insufficiently discriminating in the choice of rejected data. Since IRLS is not designed for errors-in-variables problems, this outcome is somewhat expected.

Apparatus

Figure 6:
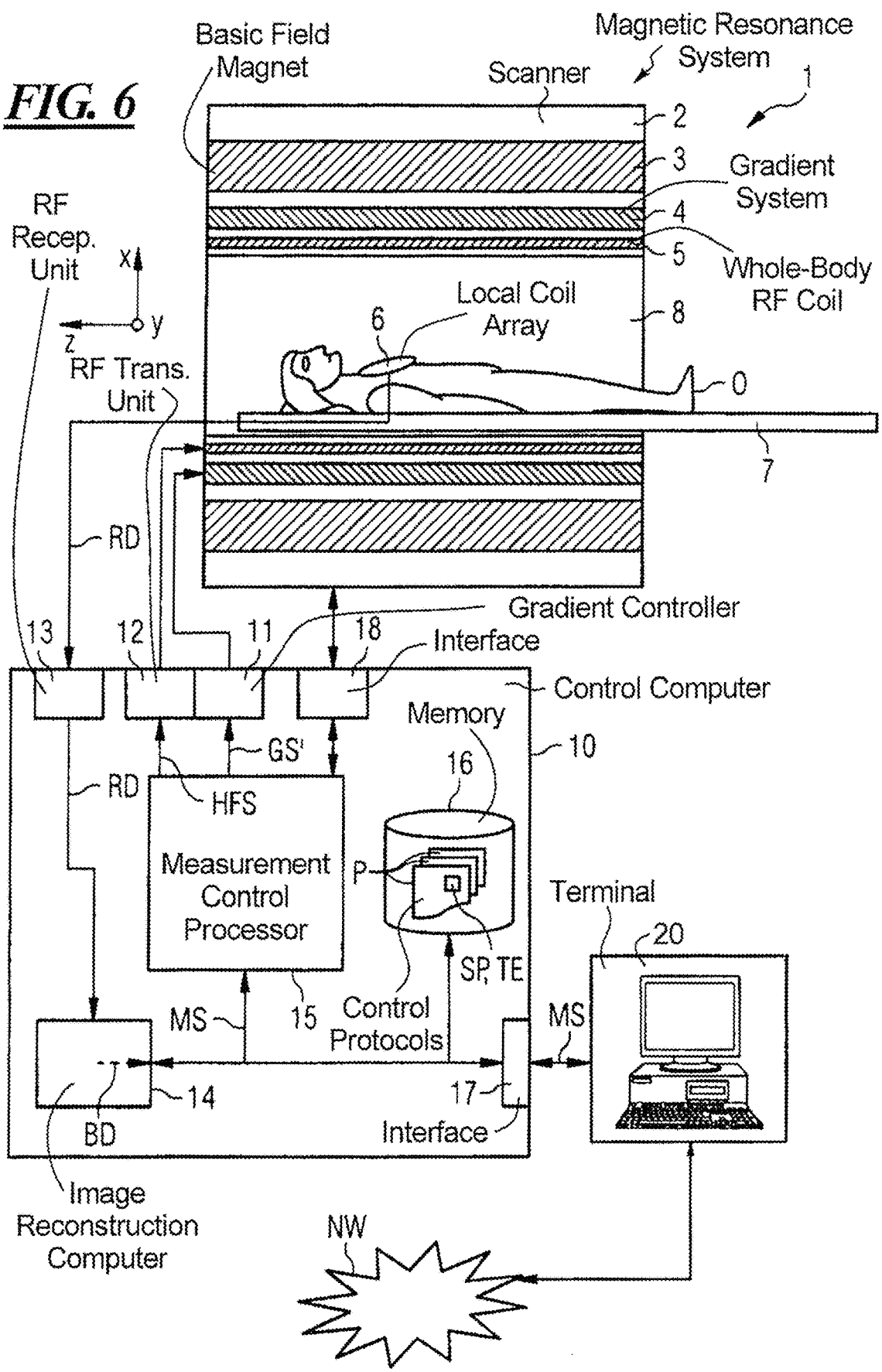
FIG. 6 is a schematic illustration of an MRI apparatus that is operable in order to implement the inventive method.

A magnetic resonance system 1 according to the invention is schematically shown in FIG. 6. It includes the actual magnetic resonance scanner 2 with an examination space or patient tunnel located therein. A bed 7 can be driven into this patient tunnel 8, such that a patient O or examination subject lying on THE bed 7 can be supported at a defined position within the magnetic resonance scanner 2 relative to the magnet system and radio-frequency system arranged therein during an examination, or can be moved between different positions during a measurement.

Basic components of the magnetic resonance scanner 2 are a basic field magnet 3, a gradient system 4 with magnetic field gradient coils to generate magnetic field gradients in the x-, y- and z-directions, and a whole-body radio-frequency (RF) antenna 5. The magnetic field gradient coils can be controlled independently of one another in the x-, y- and z-directions so that gradients can be applied in arbitrary logical spatial directions (for example in the slice-selection direction, in the phase coding direction or in the readout direction) via a predetermined combination, wherein these directions normally depend on the selected slice orientation. The transmission (radiation) of RF signals in order to induce of magnetic resonance signals in the examination subject O can take place via the whole-body antenna 5. The MR signals are received with a local coil array 6 composed of multiple individual reception coils. The local coil array 6 can also be used to radiate the RF signals. All of these components are known in principle to those skilled in the art and therefore are only schematically shown in FIG. 6.

The components of the magnetic resonance scanner 2 are controlled by a control computer, which can be formed by a number of individual computers (which may be spatially separated and connected among one another via suitable cables or the like). This control computer 10 is connected via a terminal interface 17 with a terminal 20 via which an operator can control the entire system 1. In the present case, this terminal 20 (as a computer) is equipped with keyboard, one or more monitors and additional input devices (for example mouse or the like) so that a graphical user interface is provided to the operator.

Among other things, the control computer 10 has a gradient controller 11 that can in turn have multiple sub-components. Via this gradient controller 11, the individual gradient coils are provided with control signals according to a gradient pulse sequence GS. These gradient pulses are radiated (activated) at precisely provided time positions and with a precisely predetermined time curve during a measurement.

The control computer 10 also has a radio-frequency transmission unit 12 in order to feed electrical signals respectively representing radio-frequency pulses into the whole-body radio-frequency coil 5 (or the local coil array 6) according to a predetermined radio-frequency pulse sequence RFS of the pulse sequence MS. The radio-frequency pulse sequence RFS includes excitation and/or refocusing pulses. The reception of the magnetic resonance signals then occurs with the use of the reception coils of the local coil array 6, and the raw data RF received in this manner are read out and processed by an RF reception unit 13. The magnetic resonance signals are passed in digital form as raw data RF to a reconstruction computer 14, which reconstructs the image data BD from the raw data using the reconstruction algorithm described above, and stores the image data BD in a memory 16 and/or passes the image data BD via the interface 17 to the terminal 20 so that the operator can view the image. The image data BD can also be stored at other locations via a network NW and/or be displayed and evaluated.

Control commands are transmitted via an interface 18 to other components of the magnetic resonance scanner 2 (such as the bed 7 or the basic field magnet 3, for example), and measurement values or other information are received.

The gradient control unit 11, the RF transmission unit 12 and the RF reception unit 13 are controlled, in a coordinated manner, by a measurement control processor 15. Via corresponding commands, this ensures that the desired gradient pulse sequences GS and radio-frequency pulse sequences RFS are emitted. Moreover, for this purpose it must be ensured that the magnetic resonance signals are read out by the reception coils of the local coil array 6 by the RF reception unit 13 at the appropriate point in time and are processed further. The measurement control processor 15 likewise controls the interface 18.

The basic operation of such a magnetic resonance measurement (apart from the reconstruction described above) and the cited components to control it are known to those skilled in the art, so that they need not be described in further in detail herein. Moreover, such a magnetic resonance scanner 2 and the associated control device can have an additional components that are likewise not explained in detail herein. It should also be noted that the magnetic resonance scanner 2 can also be designed differently—for example with a laterally open patient space, or as a smaller scanner in which only one body part is positioned.

In order to start a measurement, via the terminal an operator can typically select a control protocol P provided for this measurement from a memory 16 in which a number of control protocols P for different measurements are stored. Among other things, this control protocol P includes various control parameters for the respective measurement. Among these control parameters are specific basic rules for the desired pulse sequence, for example whether it is a spin echo sequence, a turbo spin echo sequence, etc. These control parameters also designated the magnetizations of nuclear spins to be achieved via the individual radio-frequency pulses, rules about the k-space trajectory to be used to enter the raw data into k-space, as well as parameters that set slice thicknesses, slice intervals, number of slices, echo time in a spin echo sequence, etc.

With the use of the terminal 20, the operator can modify a portion of these control parameters in order to create an individual control protocol for a currently desired measurement. For this purpose, variable control parameters are offered for modification at a graphical user interface of the terminal, for example.

Moreover, via a network NW the operator can retrieve control protocols (for example from a manufacturer of the magnetic resonance system 1) and may possibly modify such protocols, in order to operate the system.

Further Discussion

Motion errors in MRI data are not outliers in the classical sense but more typically manifest as phase shifts resulting from translations in the spatial domain. Such errors do not appear very different from normal data and so to identify them it is necessary to employ data consistency criteria. Parallel imaging provides one such criterion that takes advantage of the redundancy in datasets acquired by multiple coils. The potential for artifact reduction and robust parallel image reconstruction has been recognized previously, also in combination with smooth phase and object support constraints, but has been difficult to exploit for reasons outlined in the Introduction. Examples of artefact reduction have only been shown with corruption in the high spatial frequencies but not the low spatial frequencies where calibration data are located. The present invention, based on exploiting the redundancies inherent in k-space convolution (including parallel imaging and object support (Haldar et al., "Low-rank modeling of local k-space neighborhoods (LOR-AKS) for constrained MRI," IEEE Trans Med Imaging, Vol. 33(3), pp. 668-81 (2014))), has a high tolerance to errors anywhere in the data (c.f. FIGS. 3 and 5).

The idea of rejecting outliers from k-space was taken up recently using a low rank plus sparse matrix decomposition (Jin et al., "MRI Artifact Correction Using Sparse+Low-Rank Decomposition of Annihilating Filter-Based Hankel Matrix," Magnetic Resonance in Medicine (Early View 2016)). In contrast to the present invention, Jin et al. apply total variation filtering and weighting to the data prior to forming the calibration matrix, whereas the present invention does not perform weighting (or at least, only binary weighting) and applies minimum variance filtering to the singular values. As with earlier studies, Jin et al. shows examples of relatively minor motion artefacts in the high spatial frequencies.

It should be noted that the residual in accordance with the invention follows the underlying signal amplitude and the local sampling density. One plausible explanation is that the phase errors are multiplicative whereas the residual is more appropriate for an additive error. This would give rise to a residual that varies with the underlying signal; however, the dependence can also be seen in numerical phantoms without any added errors and so the structure cannot be due to this mismatch alone. Increasing the kernel size and using pea rather than summation over redundant dimensions can help reduce the signal. This can represent a challenge for accelerated scans, since the contiguously sampled center of k-space tends to exhibit large residuals and is more likely to be rejected.

As noted above, suitable a stopping rule to end the data rejection process is to set a certain predetermined fraction of the data. Rejecting a higher fraction of data can potentially increase the tolerance to artefacts but rejecting too much data (calibration or otherwise) leads to an unrecoverable problem, or at least unnecessary SNR and g-factor penalties.

The types of data corruption that are addressed by data consistency follow the paradigm of a few bad points scattered throughout a mostly good data set. This can be imposed to some extent by ordering the data acquisition incoherently (randomly or in a manner similar to (Derbyshire et al., "Golden-step phase encoding for flexible real-time Cardiac MRI," J Cardiovasc Magn Reson., Vol. 13 (Suppl 1), p. 23 (2011); Weick et al., "Desynchronization of Cartesian k-Space Sampling and Periodic Motion for Improved Retrospectively Self-Gated 3D Lung MRI Using Quasi-Random Numbers," Magnetic Resonance in Medicine, Vol. 77, pp. 787-793 (2017))) but the approach does not constitute a comprehensive solution to motion in MRI. A more realistic expectation (paraphrasing the Introduction of (Huber et al., In: Robust Statistics 2ed. (Wiley 2009))) is to better tolerate minor deviations of the assumptions that underlie image reconstruction. Methods based on linear least squares are vulnerable in the sense that MRI acquisitions lasting several minutes can be ruined by a few seconds of motion. By using more error tolerant reconstructions, it is expected that clinical scans that would normally be repeated or abandoned due to motion artefact will become diagnostically useable.

Many other complementary approaches to motion control are available based on hardware (respiratory belts, camera tracking, field monitoring, etc.), signal navigators and thermal noise navigators (Zaitsev et al., "Motion artifacts in MRI: A complex problem with many partial solutions," J Magn Reson Imaging, Vol. 42(4), pp. 887-901 (2015); Andreychenko, et al., "Thermal Noise Variance of a Receive Radiofrequency Coil as a Respiratory Motion Sensor," Magnetic Resonance in Medicine, Vol. 77, pp. 221-228 (2017)). To improve robustness to motion in clinical practice, there is no need to rely on a single strategy since each can provide an independent measure of the motion and increase the overall tolerance to non-ideal scan conditions.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for magnetic resonance (MR) image reconstruction, comprising:
   providing a computer with a plurality of undersampled k-space data sets from an MR scan, each comprising data points in a k-space matrix, in which data entries at said data points were made in each k-space data set by a parallel MR data acquisition using a plurality of reception coils, with each reception coil sampling a respective one of said k-space data sets, in which said data points in each of said k-space data sets contain errors as a result of a subject exhibiting motion during the MR scan;
   in said computer, generating a calibration matrix for an image reconstruction algorithm that uses a parallel image reconstruction technique together with a structured low rank matrix completion of said calibration matrix that requires said calibration matrix to satisfy a low rank matrix constraint, by organizing said data points in said k-space data sets in order to give said data points in said calibration matrix a Hankel structure;
   in said computer, for each data point in said calibration matrix, calculating a noise variance estimation based on the singular values of the calibration matrix;
   in said computer, subjecting said calibration matrix to an iterative rank reduction procedure in which a rank of the calibration matrix is reduced in each iteration and an iterative loop and, after each iteration, calculating a residual that is the difference between the reconstructed points and the actual acquired data points and removing data points, for a next iteration, that have a residual that is higher than a predetermined residual threshold, and repeating said iterations until a predetermined completion criterion is reached, with a last iteration, in which said completion criterion was reached, producing a low rank calibration matrix;
   in said computer, executing said parallel image reconstruction technique together with said structured low rank matrix completion using said low rank calibration matrix, in order to reconstruct an image data set of the subject; and
   making the reconstructed image data of the subject available from the computer in electronic form as a data file.

2. A method as claimed in claim 1 comprising generating said low rank calibration matrix by applying a filter to each data point in said data matrix, said filter transitioning between a low noise variance and a high noise variance.

3. A method as claimed in claim 1 comprising rejecting and replacing, as said completion criterion, an occurrence of a predetermined fraction of a total number of data points that were originally present in said calibration matrix.

4. A method as claimed in claim 1 comprising in said computer, making use of separately acquired calibration data that contains no motion-related errors in order to remove a singular value decompression computation outside the iterative loop.

5. A method as claimed in claim 1 comprising, in said computer, making use redundancy in the data to detect errors that are expressed by a low rank structured matrix constraint, the redundancy including at least one of object support in the spatial domain and conjugate symmetry in the k-space domain.

6. The method as claimed in claim 1, wherein the residual that is the difference between the reconstructed points and the actual acquired data points represents an indication of satisfaction of the respective data points with the low rank matrix constraint.

7. The method as claimed in claim 6, wherein the predetermined residual threshold identifies data points to be removed during each iteration that least satisfy the low rank matrix constraint.

8. The method as claimed in claim 1, wherein upon reaching the predetermined completion criterion and producing the low rank calibration matrix, the resulting image data set of the subject includes less errors as a result of the subject exhibiting motion during the MR scan than an original resulting image data set generated using the data points in each of said k-space data sets.

9. The method as claimed in claim 1, wherein the predetermined completion criterion specifies a predetermined proportion of data points that are to be maintained in the calibration matrix upon reaching the last iteration.

10. A computer for magnetic resonance (MR) image reconstruction, comprising:
a processor provided with a plurality of undersampled k-space data sets from an MR scan, each comprising data points in a k-space matrix, in which data entries at said data points were made in each k-space data set by a parallel MR data acquisition using a plurality of reception coils, with each reception coil sampling a respective one of said k-space data sets, in which said data points in each of said k-space data sets contain errors as a result of a subject exhibiting motion during the MR scan;
said processor being configured to generate a calibration matrix for an image reconstruction algorithm that uses a parallel image reconstruction technique together with a structured low rank matrix completion of said calibration matrix that requires said calibration matrix to satisfy a low rank matrix constraint, by organizing said data points in said k-space data sets in order to give said data points in said one calibration matrix a Hankel structure;
said processor being configured to calculate, for each data point in the calibration matrix, a noise variance estimation based on the singular values of the calibration matrix;
said processor being configured to subject said calibration matrix to an iterative rank reduction procedure in which a rank of the calibration matrix is reduced in each iteration in an iterative loop and, after each iteration, calculate a residual that is the difference between the reconstructed points and the actual acquired data points for each data point and remove data points, for a next iteration, that have a residual that is higher than a predetermined residual threshold, and to repeat said iterations until a predetermined completion criterion is reached, with a last iteration, in which said completion criterion was reached, producing a low rank calibration matrix;
said processor being configured to execute said parallel image reconstruction technique together with said structured low rank matrix completion using said low rank calibration matrix, in order to reconstruct an image data set of the subject; and
said processor being configured to make the reconstructed image data of the subject available from the processor in electronic form as a data file.

11. A computer as claimed in claim 10 wherein said processor is configured to generate said low rank calibration matrix by applying a filter to the singular values of said calibration matrix, said filter transitioning between low values and high values.

12. A computer as claimed in claim 10 wherein said processor is configured to reject and replace, using said matrix completion criterion, an occurrence of a predetermined fraction of a total number of data points that were originally present in said calibration matrix.

13. A computer as claimed in claim 10 wherein said processor is configured to make use of separately acquired calibration data that contains no motion-related errors in order to remove a singular value decomposition computation outside of the iterative loop.

14. A computer as claimed in claim 10 wherein said processor is configured to use redundancy in the data to detect errors that are expressed by a low rank structured matrix constraint, the redundancy including at least one of object support in the spatial domain support and conjugate symmetry in the k-space domain.

15. A magnetic resonance (MR) apparatus comprising:
an MR data acquisition scanner comprising a plurality of reception coils;
a computer configured to operate the MR data acquisition scanner in order to perform an MR scan to acquire a plurality of undersampled k-space data sets, each comprising data points in a k-space matrix, in which data entries at said data points were made in each k-space data set by a parallel MR data acquisition using said plurality of reception coils, with each reception coil sampling a respective one of said k-space data sets, in which said data points in each of said k-space data sets contain errors as a result of a subject exhibiting motion during the MR scan;
said computer being configured to generate a calibration matrix for an image reconstruction algorithm that uses a parallel image reconstruction technique together with a structured low rank matrix completion of said calibration matrix that requires said calibration matrix to satisfy a low rank matrix constraint, by organizing said data points in said k-space data sets in order to give said data points in said one calibration matrix a Hankel structure;
said computer being configured to calculate, for each data point in said data matrix, a noise variance estimation and to calculate a residual that is a difference between the estimated data point and an actual value of the respective data point, with said residual being a measure of how poorly the respective data point satisfies said low rank matrix constraint;
said computer being configured to subject said calibration matrix to an iterative rank reduction procedure in which a rank of the calibration matrix is reduced in each iteration in an iterative loop and, after each iteration, to calculate said residual for each data point and remove data points, for a next iteration, that have a residual that is higher than a predetermined residual threshold, and to repeat said iterations until a predetermined completion criterion is reached, with a last iteration, in which said completion criterion was reached, producing a low rank calibration matrix;

said computer being configured to execute said parallel image reconstruction technique together with said structured low rank matrix completion using said low rank calibration matrix, in order to reconstruct an image data set of the subject; and said computer being configured to make the reconstructed image data of the subject available from the computer in electronic form as a data file.

16. An MR apparatus as claimed in claim 15 wherein said computer is configured to generate said low rank calibration matrix by applying a filter to each data point in said data matrix, said filter transitioning between low values and high values.

17. An MR apparatus as claimed in claim 15 wherein said computer is configured to reject and replace, using said completion criterion, an occurrence of a predetermined fraction of a total number of data points that were originally present in said data matrix.

18. An MR apparatus as claimed in claim 15 wherein said computer is configured to make use of separately acquired calibration data that contains no motion-related errors in order to remove a singular value decomposition computation outside of the iterative loop.

19. An MR apparatus as claimed in claim 15 wherein said computer is configured to use redundancy in the data to detect errors that are expressed by a low rank structured matrix constraint, the redundancy including at least one of object support in the spatial domain and conjugate symmetry in the k-space domain.

20. A non-transitory, computer-readable data storage medium encoded with programming instructions, said storage medium being loaded into a computer and said programming instructions causing said computer to:

receive a plurality of undersampled k-space data sets from a magnetic resonance (MR) scan, each comprising data points in a k-space matrix, in which data entries at said data points were made in each k-space data set by a parallel MR data acquisition using a plurality of reception coils, with each reception coil sampling a respective one of said k-space data sets, in which said data points in each of said k-space data sets contain errors as a result of a subject exhibiting motion during the MR scan;

generate one calibration matrix for an image reconstruction algorithm that uses a parallel image reconstruction technique together with a structured low rank matrix completion of said calibration matrix that requires said calibration matrix to satisfy a low rank matrix constraint, by organizing said data points in said k-space data sets in order to give said data points in said calibration matrix a Hankel structure;

for each data point in said calibration matrix, calculate a noise variance estimation from the singular values;

subject said calibration matrix to an iterative rank reduction procedure in which a rank of the calibration matrix is reduced in each iteration and, after each iteration in an iterative loop, calculate a residual that is the difference between the reconstructed points and the actual acquired data points and remove data points, for a next iteration, that have a residual that is higher than a predetermined residual threshold, and repeat said iterations until a predetermined completion criterion is reached, with a last iteration, in which said completion criterion was reached, producing a low rank calibration matrix;

execute said parallel image reconstruction technique together with said structured low rank matrix completion using said low rank calibration matrix, in order to reconstruct an image data set of the subject; and make the reconstructed image data of the subject available from the computer in electronic form as a data file.

21. A data storage medium as claimed in claim 20 wherein said programming instructions cause said computer to generate said low rank calibration matrix by applying a filter to the singular values of said calibration matrix, said filter transitioning between low values and high values.

22. A data storage medium as claimed in claim 20 wherein said programming instructions cause said computer to reject and replace, as said completion criterion, an occurrence of a predetermined fraction of a total number of data points that were originally present in said calibration matrix.

23. A data storage medium as claimed in claim 20 wherein said programming instructions cause said computer to use separately acquired calibration data that contains no motion-related errors in order to remove a singular value decomposition computation outside the iterative loop.

24. A data storage medium as claimed in claim 20 wherein said programming instructions cause said computer to use redundancy in the data to detect errors that are expressed by a low rank structured matrix constraint, the redundancy including at least one of object support in the spatial domain and conjugate symmetry in the k-space domain.

* * * * *